United States Patent [19]
Lee et al.

[11] Patent Number: 6,086,599
[45] Date of Patent: Jul. 11, 2000

[54] MICRO DEVICES USING SHAPE MEMORY POLYMER PATCHES FOR MATED CONNECTIONS

[75] Inventors: Abraham P. Lee, Walnut Creek; Joseph P. Fitch, Livermore, both of Calif.

[73] Assignee: The Regents of the University of California, Oakland, Calif.

[21] Appl. No.: 09/246,878

[22] Filed: Feb. 8, 1999

[51] Int. Cl.[7] .................................................. A61B 17/00
[52] U.S. Cl. ............................................................ 606/108
[58] Field of Search ............................... 606/1, 108, 195, 606/209, 106, 192, 194, 200, 198; 623/1, 12; 294/145, 165; 128/DIG. 15; 428/100; 403/381

[56] References Cited

U.S. PATENT DOCUMENTS

| | | | |
|---|---|---|---|
| 3,590,414 | 7/1971 | Gores | 128/DIG. 15 |
| 4,290,174 | 9/1981 | Kalleberg | 428/100 |
| 5,474,563 | 12/1995 | Myler et al. | 606/108 |
| 5,562,641 | 10/1996 | Flomenblit et al. | 623/1 |
| 5,630,671 | 5/1997 | Larson | 403/28 |
| 5,645,564 | 7/1997 | Northrup et al. | 606/205 |
| 5,911,737 | 6/1999 | Lee et al. | 606/209 |

*Primary Examiner*—Gene Mancene
*Assistant Examiner*—Eduardo C. Robert
*Attorney, Agent, or Firm*—L. E. Carnahan; Alan H. Thompson

[57] ABSTRACT

A method and micro device for repositioning or retrieving miniature devices located in inaccessible areas, such as medical devices (e.g., stents, embolic coils, etc.) located in a blood vessel. The micro repositioning or retrieving device and method uses shape memory polymer (SMP) patches formed into mating geometries (e.g., a hoop and a hook) for re-attachment of the deposited medical device to a catheter or guidewire. For example, SMP or other material hoops are formed on the medical device to be deposited in a blood vessel, and SMP hooks are formed on the micro device attached to a guidewire, whereby the hooks on the micro device attach to the hoops on the medical device, or vice versa, enabling deposition, movement, re-deposit, or retrieval of the medical device. By changing the temperature of the SMP hooks, the hooks can be attached to or released from the hoops located on the medical device. An exemplary method for forming the hooks and hoops involves depositing a sacrificial thin film on a substrate, patterning and processing the thin film to form openings therethrough, depositing or bonding SMP materials in the openings so as to be attached to the substrate, and removing the sacrificial thin film.

25 Claims, 4 Drawing Sheets

MICRO DEVICES USING SHAPE MEMORY POLYMER PATCHES FOR MATED CONNECTIONS

The United States Government has rights in this invention pursuant to Contract No. W-7405-ENG-48 between the United States Department of Energy and the University of California for the operation of Lawrence Livermore National Laboratory.

BACKGROUND OF THE INVENTION

The present invention relates to the deposition of devices, such as medical devices, in inaccessible locations, such as blood vessels, particularly to a micro device for repositioning or retrieval of deposited devices, and more particularly to a micro device using shape memory polymer patches for re-attaching to such a deposited device to enable repositioning or retrieval thereof, and to a method for fabricating the micro device. There are medical applications which require the release of a device (e.g., stent, embolic coil) into a blood vessel usually through a catheter or attached to an end of a guidewire. Accurate placement of the device in the blood vessel is usually critical both for a good outcome and to avoid severe complications (e.g., downstream emboli). Unfortunately, the pulsatile flow of blood through the vessels often moves the device as the positioning system is detached or released therefrom and removed from the body. The situation is compounded by the higher pressures from increased blood flow as the catheter, for example, is removed from the area and less of the vessel's volume is blocked. Because it is not possible to directly visualize the devices, x-ray shadowgrams (or angiograms) are used, and because the volumes are small (millimeter and smaller blood vessels), finding and attaching to a released device is very difficult.

Similar type problems exist in the non-medical field, wherein, for example, components are assembled inside of complex machinery that cannot be opened, or material, such as filters, etc., must be deposited in inaccessible locations.

Thus, there exists a need for a means by which material or devices can be deposited in inaccessible locations, and if need be, repositioned or retrieved. This need is particularly applicable for medical applications involving the deposit of medical materials or devices at a critical location in a blood vessel, etc.

The present invention provides a solution to the above-referenced problems by providing a micro device which can be re-attached to a previously deposited medical device, for example, for repositioning or retrieval thereof. In addition, the micro device can be utilized to initially deposit the medical device. Thus, the present invention enables the use of a single micro device to deposit, reposition, or retrieve a medical device, for example, in a blood vessel. This is accomplished, for example, by the formation of hoops on the medical device and the formation of shape memory polymer (SMP) hooks on the micro device, whereby the SMP hooks and deposits a medical device by release of the hooks from the hoops on the medical device, or re-attach the hooks to the hoops of the medical device for repositioning or retrieval thereof. The SMP hooks are activated by heating to cause release of the hoops or by heating and cooling to cause re-attachment to the hoops.

SUMMARY OF THE INVENTION

It is an object of the present invention to provide a micro device capable of at least re-attachment to a device located in an inaccessible area (or other packaging solutions) for repositioning or retrieving the device.

A further object of the invention is to provide a micro device which incorporates shape memory polymer material by attachment and release of a medical or non-medical device.

A further object of the invention is to provide a device incorporating microshape memory polymer patches for mated connections.

Another object of the invention is to provide a micro device using shape memory polymer material for attachment to and release of a device located in an inaccessible area.

Another object of the invention is to provide a micro device capable of releasing, re-attaching, and re-releasing a medical or non-medical device using shape memory polymer materials.

Another object of the invention is to provide mated connections on a retaining/releasing device and a device to be retained/released which utilizes a series of hoops and hooks which can be attached, released, and re-attached by heating and cooling of at least the hooks.

Another object of the invention is to provide mated connections composed of hooks and hoops wherein at least the hooks are composed of shape memory polymer material.

Another object of the invention is to provide a method for fabricating mated connections composed of hooks and hoops, wherein at least the hooks are composed of shape memory polymer material.

Other objects and advantages of the present invention will become apparent from the following description and accompanying drawings. The invention involves a method and micro device using shape memory polymer (SMP) material for mated connections on a device to be deposited and a device capable of depositing, repositioning, or retrieval of the device to be deposited. The invention, for example, solves the above-referenced problem of re-attaching to a medical device that has been previously deposited in a blood vessel. The re-attachment allows the medical device to be repositioned for better medical outcome. The invention uses two mating geometries, such as hoops on the medical device and hooks on the re-attachment device, with at least the hooks being composed of SMP materials. Re-attachment and release of the hooks/hoops is accomplished by appropriately changing the temperature of the SMP material so as to change the properties or relax the "memory" properties using thermal heating (light, electrical, fluid, high frequency). The hook/hoop arrangement is produced by conventional technology. the invention is a "sticky" guidewire that can be attached to a medical device, for example, at an arbitrary angle, and this allows a released device to be recaptured without precise alignment with the recapturing device.

BRIEF DESCRIPTION OF THE DRAWINGS

The accompanying drawings, which are incorporated into and form a part of the disclosure, illustrate embodiments of the invention and, together with the description, serve to explain the principles of the invention.

DETAILED DESCRIPTION OF THE INVENTION

Figure 1:
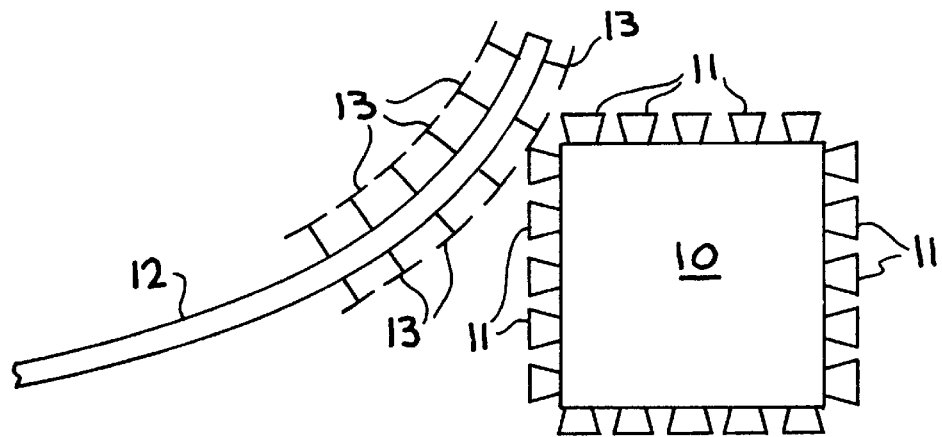
FIG. 1 illustrates a greatly enlarged embodiment of the invention using hoops on a device and SMP hooks on a guidewire.

The present invention is directed to a micro device using shape memory polymer (SMP) material in mated connections for retaining, releasing, re-attaching, and re-releasing of a device located in an inaccessible location and thus constitutes a "sticky" guidewire. As pointed out above, it is often necessary to position or re-position a medical device in a blood vessel. This invention solves the prior problem of re-attaching a medical device to a delivery device, such as a guidewire or catheter to enable re-positioning the medical device or for retrieval thereof. By this invention, two mating geometries are provided with the medical device being provided with hoops, which may be made of SMP or other materials, and the delivery device being provided with hooks composed of SMP material. Attachment or re-attachment of the delivery device to the medical device is accomplished by appropriately changing the temperature of the SMP hooks whereby they can be attached to the hoops of the medical device, and thereafter again changing the temperature of the SMP hooks whereby release of the hoops is accomplished by relaxing the "memory" properties of the SMP hooks, using thermal heating (light, electrical, fluid, high frequency).

SMP material is known in the art, and has been recently utilized as delivery means for medical or non-medical devices to inaccessible locations, such as blood vessels or inside a machine or tubing system. These recent applications of SMP material for delivery means are exemplified by copending U.S. applications Ser. No. 08/807,412 filed Feb. 28, 1997, entitled "Microfabricated Therapeutic Actuators", now U.S. Pat. No. 5,911,737 issued Jun. 15, 1999 and Ser. No. 09/067,824, filed Apr. 28, 1998, entitled "Microfabricated Therapeutic Actuators and Release Mechanisms Therefor", each assigned to the same assignee. SMP materials, manufactured by Mitsubishi LTD, can be formed into various configurations and sizes, as well as being deposited in selected areas or openings, and thus can be manufactured as small diameter microtubing of various diameters or in sheets of varying thickness. SMP is a polyurethane-based material that undergoes a phase transformation at a manufactured temperature, Tg. As the material is polymerized (cross-linked), the material is molded or formed into its memory shape. At a temperature above the Tg, the material is soft and can easily be arbitrarily reshaped into another configuration by applying pressure. The elastic constant of the material can change by about 200 times when undergoing this phase transformation. As the temperature is lowered, with the pressure applied, to a temperature below the Tg, this new shape is fixed and locked in as long as the material stays below the Tg. However, if the temperature reheats the material to above the Tg, the material will return to its original "memory" shape. The SMP material can be heated thermally, resistively, optically, high frequency, or by heated fluid. Thus, by utilizing SMP material having a specified manufacture temperature, Tg, the material will soften and can be reshaped above the Tg and harden below the Tg to maintain that reshape, until it is reheated to a temperature above the Tg whereby it reverts to its "memory" shape. It is readily seen that by forming two mating geometries, hooks and hoops, or at least the hooks from SMP material, the hooks, when heated above their Tg, can attach to, cool, and retain the hoops until the hooks are again heated above their Tg, where the hooks release the hoops when the SMP material relaxes or reverts to its "memory" shape.

The "sticky" guidewire of this invention can be attached to a medical device at an arbitrary angle. This allows a released device to be recaptured without having to precisely align holes and latches. In order to re-release the device, the SMP material is heated using light, electricity, high frequency, or fluid to a temperature above the Tg thereof so that the SMP material loses its "mechanical" stickiness. Examples of the medical device, the SMP geometry, and potential SMP manufacturing approaches are described hereinafter.

As shown in FIG. 1, a greatly enlarged medical device 10 is coated with a large number or array of micro hoops 11. The hoops 11 do not need to be made of SMP material or to have actuation properties, but can be. A "sticky" guidewire or tool 12 is coated with a large number or array of micro hooks 13 that are constructed of SMP material and can be heated and cooled to attach or re-attach or relaxed for release by heating to above the temperature Tg, as described above. When the two materials 11 and 13 are in contact, the spatially dense arrays allow a strong bond to form. For example, there may be up to about 2500 hoops 11 and hooks 13 per inch. Because the materials of the hoops 11 and hooks 13 conform both to the shape of the medical device 10 and the guidewire 12, precise alignment is not needed and the device and guidewire are not significantly larger than uncoated counterparts.

Figure 2:
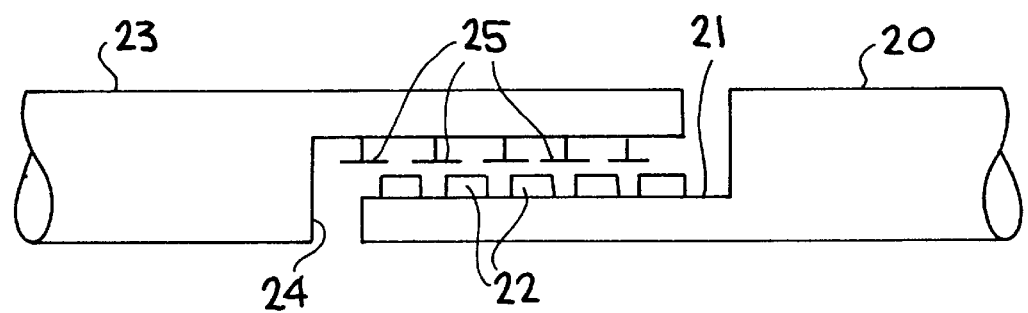
FIG. 2 illustrates an enlarged side view of another embodiment of the invention utilizing mated connections of hoops and hooks.

FIG. 2 illustrates a side view of another embodiment of the invention wherein a medical device 20, which may be of a cylindrical shape, is provided with a cutaway section 21 on which an array of hoops 22 are secured; and an end section of a guidewire, tool, or catheter 23, which may also be cylindrical, having a cutaway section 24 on which an array of hooks 25 are secured to cooperate with the hoops 22 of device 20, as described above.

For intravascular neural applications the SMP geometry requires thousands of hooked SMP filaments (hoops and hooks) per square inch since the smallest blood vessel would be less than 1 mm in diameter. Using micro-machining techniques described below, hooked SMP filaments could be placed as close as 10 $\mu$m apart, providing a very dense array of mating filaments (2500 filaments/inch).

Figure 3A:
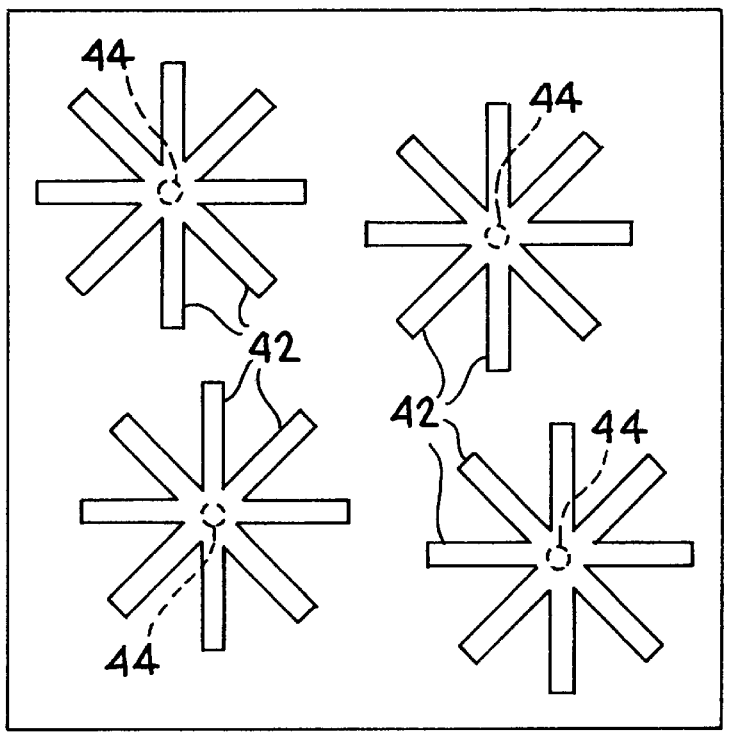
FIGS. 3A, 3B, and 3C and FIGS. 4A, 4B, and 4C illustrate top views and cross-sections of substrates along a centerline processed by a method for fabricating SMP hooks and hoops, for use as shown in the embodiments of FIGS. 1 and 2.
Figure 3B:
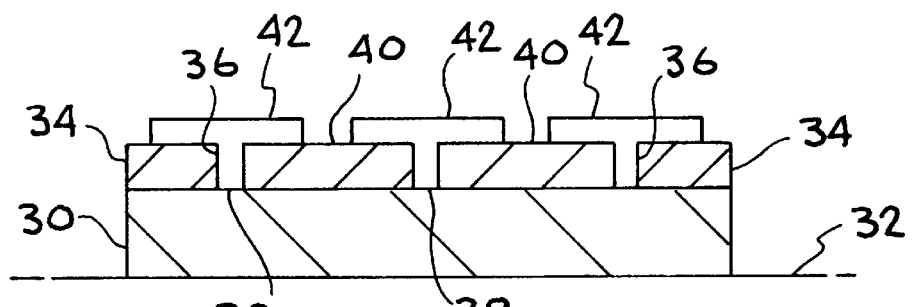
Figure 3C:
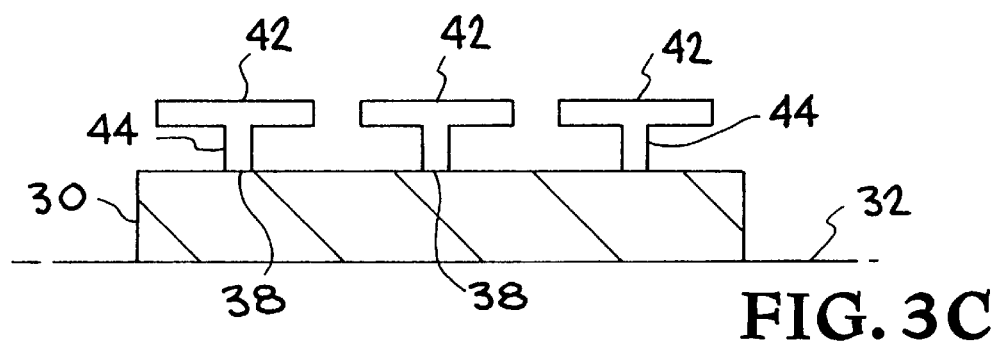
Figure 4A:
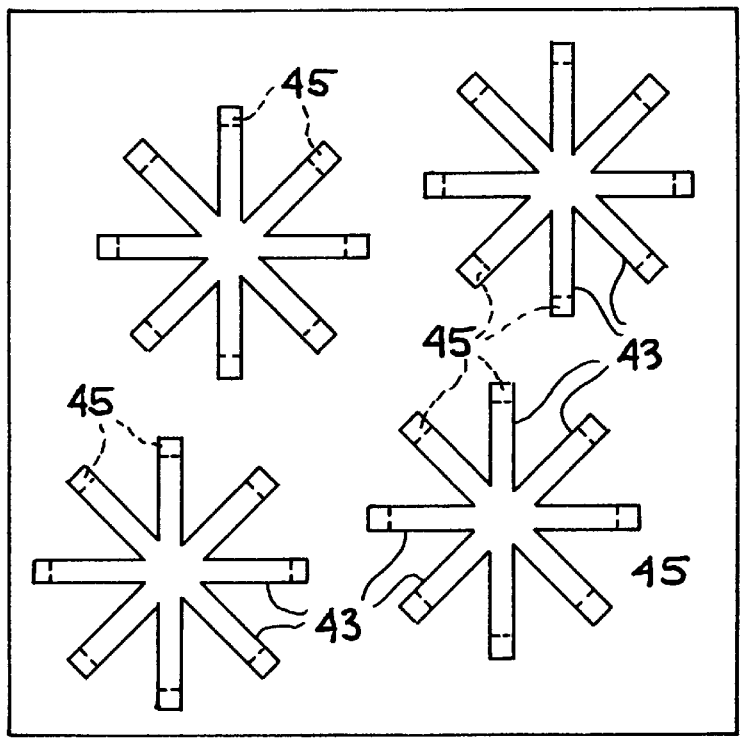
Figure 4B:
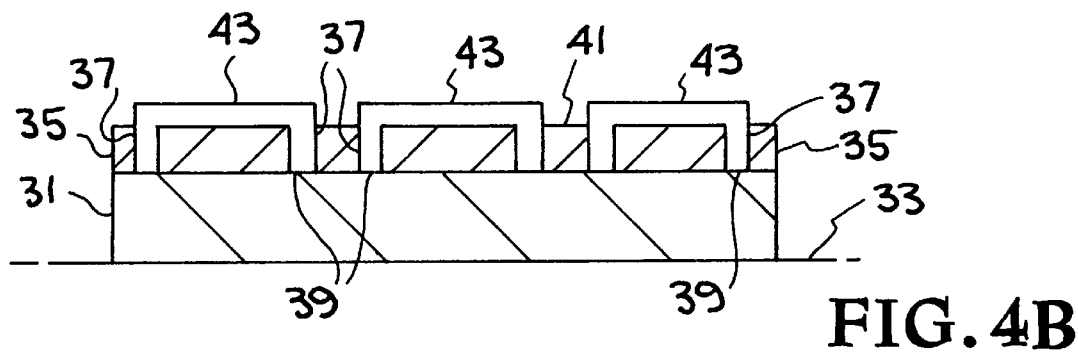

Potential manufacturing approaches include using micro-machining processes similar to those utilized in integrated circuitry fabrication. Using photolithography and surface thin film deposition techniques, one can create mating surfaces with SMP hooks and hoops. FIGS. 3A and 4A illustrate top views of hooks and hoops made by a simple processing sequence illustrated in FIGS. 3B–3C and 4B–4C which only shows a cross-section through one half of the devices of FIGS. 3A and 4A, and illustrates a simple processing sequence, as follows:

1. Provide a pair of substrates 30 and 31 as shown in FIGS. 3B and 4B, which may be of a cylindrical configuration extending around centerlines 32 and 33, for example, and composed of silicon, glass, metal, or polymer. 2. Deposit on the substrates 30 and 31, sacrificial thin films 34 and 35, which may be composed of $SiO^2$, nickel, or aluminum having a thickness of 0.5 $\mu$m to 5 $\mu$m, a shown in FIGS. 3B and 4B.

3. Lithographically patterning and processing the films 34 and 35 to form openings or vias 36 and 37 therein to form anchoring points 38 and 39 at the outer surface of substrates 30 and 31, as shown in FIGS. 3B and 4B, with openings or vias 36 and 37 having a diameter of 1.0 $\mu$m to 5.0 $\mu$m.

4. Deposit thin film shape memory polymer material in the openings or vias 36 and 37 and on the surface 40 and 41 of films 34 and 35, and pattern by lithography to form hooks 42 and hoops 43, as shown in FIGS. 3B and 4B.

Figure 4C:
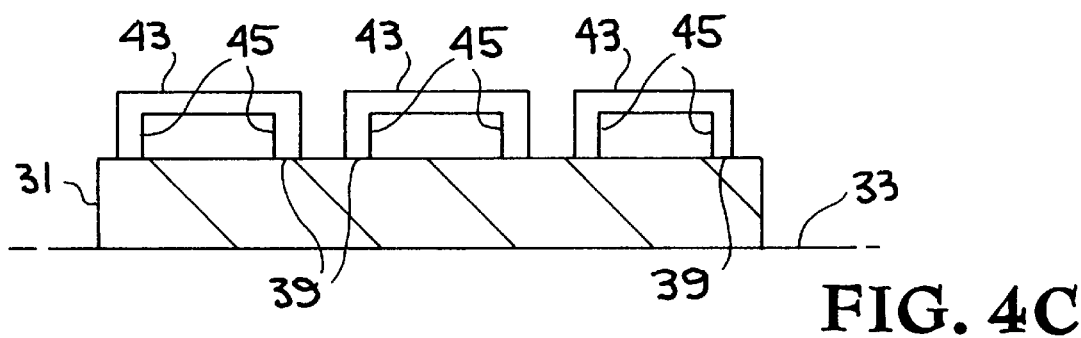

5. Selectively etch away the sacrificial thin films 34 and 35 without etching the SMP hooks 42 and hoops 43 or the substrates 30 and 31, whereby the hooks 42 and hoops 43 extend from substrates 30 and 31, as shown in FIGS. 3C and 4C. The hooks 42 of FIG. 3A have an internal anchor 44 formed by the SMP material in the openings or vias 36 or FIG. 3B, while the hoops 43 of FIG. 4A have external anchors 45 formed by the SMP material in the openings or vias 37 of FIG. 4B. Note that the hooks and hoops may be formed around the outer surface of the substrates 30 and 31, as shown in FIG. 1 or only on a selected surface of the substrates as shown in FIG. 2.

The SMP hooks 42 and hoops 43 are fabricated by the same process but with different masks and patterns. The dimension of the hooks could be as small as about 5 $\mu$m nominal in the cross-section. For three dimensional devices, one could use laser pantography to define "sticky" surfaces on the side walls of these devices.

Figure 5A:
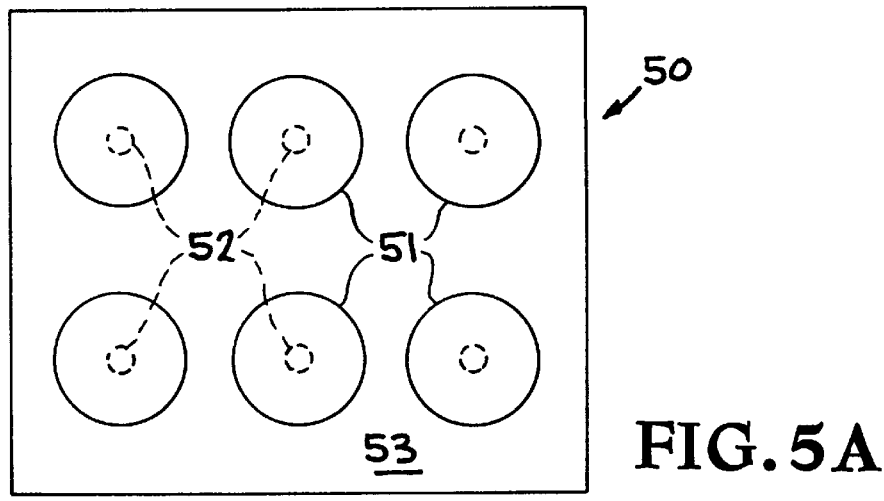
FIGS. 5A, 5B, and 5C illustrate a top view, an unconnected side view and a connected side view of anther embodiment using two mushroom shaped arrays of SMP material connectors.
Figure 5B:
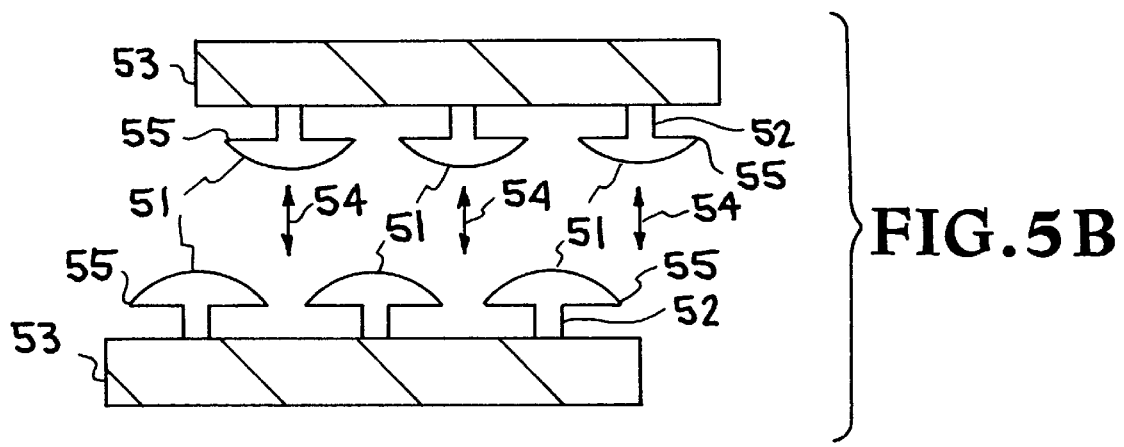
Figure 5C:
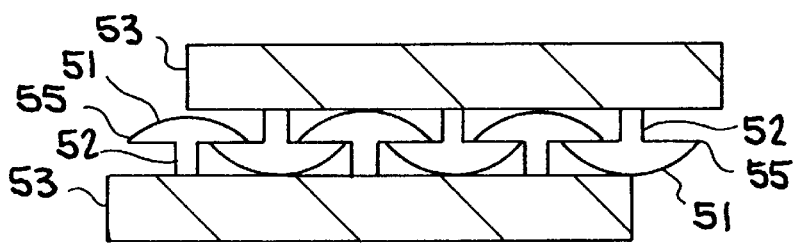

FIGS. 5A, 5B and 5C illustrate SMP mushroom configured arrays where a tight snap fit between two adjacent arrays can mate two surfaces strongly, whereas they can be separated by heating the SMP arrays above the transition temperature (Tg) of the SMP material, as described above. FIG. 5A illustrates a top view of one of the two SMP mushroom configured arrays, with FIGS. 5B illustrating in cross-section two arrays as in FIG. 5A positioned to be mated together, and with FIG. 5C showing in cross-section the two mated arrays. The SMP arrays of FIGS. 5A–5C may be fabricated by a process similar to that described above.

As seen in FIG. 5A, an array 50 of SMP members 51 are connected by anchors 52 to a substrate, member, catheter, etc., 53, the SMP members 51 each being of a mushroom or umbrella configuration with the stem defining the anchor 52. As seen in FIG. 5B a pair of substrates 53 having SMP members 51 thereon are mounted in a facing relation, whereby movement of the SMP members 51 of one substrate 53 towards the opposite substrate, as indicated by arrows 54 causes the periphery 55 of the SMP members to bend slightly allowing a light snap fit therebetween, as illustrated in FIG. 5C, thereby securing the substrates 53 together. To release the substrates from one another, the SMP members 51 on either or both of substrates 53 are heated to a temperature above the transition temperature Tg of the SMP material, thereby allowing the periphery of the adjacent SMP members to bend allowing the substrates 53 to be separated as indicated by the arrows 54. However, after separation of the substrates 53 the peripheries 55 of the SMP members will remain in a bend position until pressure is applied thereto while heated to return the peripheries 55 to the shape shown. If desired, the members 51 on only one of the substrates 53 may be composed of SMP material.

It has thus been shown that the present invention provides a method and means for depositing, releasing, re-attaching, and repositioning or retrieving micro devices, such as stents, embolic coils, parts, etc., in inaccessible locations, such as blood vessels and inside complex machinery that cannot be opened. By the use of hooks made of SMP materials and hoops made of SMP or other materials, the hooks can be heated, cooled and reheated, as described above, to enable re-attachment of a device having hoops thereon for repositioning or retrieval of the device. Thus accurate positioning of medical devices in a blood vessel may be accomplished even in view of the prior problems associated with movement of the device upon its release from a delivery device due to pulsatile flow of the blood in the vessel.

While particular embodiments of the invention have been described and illustrated, a particular fabrication sequence has been set forth, and with exemplary materials and parameters having been set forth to exemplify and teach the principles of the invention, such are not intended to be limiting. Modifications and changes may become apparent to those skilled in the art, and it is intended that the invention be limited only by the scope of the appended claims.

What is claimed is:

1. A method for attaching devices to enable repositing the devices or retrieving the devices from inaccessible locations, comprising:

forming two mating geometries on at least one surface of each of a device to be delivered and a tool, forming the mating geometry on at least the tool from shape memory polymer (SMP) material, heating of the SMP material above its temperature Tg enables mating of the two geometries and attachment of the device to the tool, followed by cooling of the SMP material below the temperature Tg to fixedly secure the device to the tool, whereby the device can be repositioned or retrieved.

2. The method of claim 1, additionally including, positioning the device in an inaccessible location, releasing the device from the tool, re-attaching the device to the tool via the two mating geometries, repositioning the device, and releasing the device at the repositioned location, whereby the releasing, re-attaching, and releasing operations are carried out by appropriate heating, cooling, and reheating of the SMP material.

3. The method of claim 1, wherein forming of the mating geometries is carried out by forming hooks on the tool and hoops on the device.

4. The method of claim 3, wherein the forming of the hooks and hoops is carried out by:

providing a pair of substrates, forming a sacrificial film on at least a surface of each substrate, forming openings in each of the sacrificial films, depositing SMP material in the openings and on the surface of the sacrificial films, patterning the deposited SMP material on each of the sacrificial films, and etching away the sacrificial material thereby producing hooks on one of the pair of substrates and hoops on another of the pair of substrates.

5. The method of claim 3, wherein the hooks and hoops are formed to have a density of up to 2500 mating geometries per inch.

6. The method of claim 3, wherein the hooks are formed to have a cross-section of about 5 $\mu$m and greater.

7. The method of claim 3, wherein the hooks are formed about 10 $\mu$m apart.

8. The method of claim 1, wherein forming of the mating geometries is carried out by forming mushroom-shaped members on the tool and the device.

9. A combination of an object and a device for delivering an object to the inaccessible location, releasing the object, re-attaching the object, and repositioning and releasing the object, or retrieving the object wherein:

said device and said object each being provided with material having multiple mating geometries, the material of the multiple mating geometries on at least said device being composed of a shape memory polymer, whereby the releasing re-attaching, and releasing of said object are carried out by appropriate heating, cooling, and reheating of the shape memory polymer.

10. The device of claim 9, wherein said mating geometries form mating filaments of a density of up to 2500/inch.

11. The device of claim 10, wherein said mating filaments are about 10 μm apart.

12. The device of claim 11, wherein said mating filaments have a cross-section of about 5 μm.

13. The device of claim 9, wherein said mating geometries comprises hooks and hoops, with the hoops being located on the device and the hooks being located on the object, or vice versa.

14. The device of claim 13, wherein said hooks have a cross-section of at least about 5 μm.

15. The device of claim 13, wherein said hooks are spaced apart by a distance of about 10 μm.

16. The device of claim 13, wherein said hooks and hoops have a density of up to 2500/inch.

17. The device of claim 9, wherein said mating geometrics comprises arrays of mushroom-shaped members located on each of the device and object.

18. A combination of a deposited device and a tool the for re-attaching and repositioning or retrieval of the deposited device, comprising:

a deposited device having connector means extending from at least one surface, a tool having connector means extending from at least one surface, at least said connector means on either the device or the tool, being formed of a shape memory polymer SMP material, whereby upon contact of said tool with said deposited device, said connector means are heated above a temperature Tg whereby by said connector means are mated together, whereafter at least said connector means on said tool are cooled to below the temperature Tg and the connector means are mated whereby the tool and deposited device are attached, after which the tool can be moved to reposition or retrieve the deposited device, and if repositioned the connector means are heated to above the temperature Tg and the mating of the connector means is withdrawn and the deposited device released from the tool at the repositioned location.

19. The combination of claim 18, wherein said connector means on said tool comprised a plurality of hooks and wherein said connector means on said device comprises a plurality of hoops, or vice versa.

20. The combination of claim 19, wherein said hooks have a cross-section of about 5 μm or greater.

21. The combination of claim 19, wherein said hooks are spaced apart a distance of about 10 μm.

22. The combination of claim 19, wherein said hooks and said hoops have a density of up to about 2500/inch.

23. The combination of claim 19, wherein both the hooks and hoops are composed of SMP materials.

24. The combination of claim 19, wherein the connector means on each the device and the tool are of a mushroom-shaped configuration.

25. The combination of claim 24, wherein all of the mushroom-shaped members are composed of SMP materials.

* * * * *